United States Patent
Collin et al.

(10) Patent No.: US 9,546,159 B2
(45) Date of Patent: Jan. 17, 2017

(54) N-SUBSTITUTED 3,4-BIS (CATECHOL) PYRROLE COMPOUNDS, AND THE PREPARATION AND USE THEREOF IN THE TREATMENT OF CANCER

(71) Applicant: Centre National De La Recherche Scientifique (CNRS), Paris (FR)

(72) Inventors: Pascal Collin, Buc (FR); Maxim Egorov, Bouguenais (FR); Bernard Delpech, Clamart (FR); Joanna Bakala, Paris (FR); Maria Achab, Gif s/Yvette (FR); Jérome Bignon, Le Val Saint Germain (FR); Odile Thoison, Palaiseau (FR); Michel Benechie, Gif s/Yvette (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 14/435,768

(22) PCT Filed: Oct. 14, 2013

(86) PCT No.: PCT/EP2013/071445
§ 371 (c)(1),
(2) Date: Jul. 2, 2015

(87) PCT Pub. No.: WO2014/060366
PCT Pub. Date: Apr. 24, 2014

(65) Prior Publication Data
US 2015/0344460 A1    Dec. 3, 2015

(30) Foreign Application Priority Data
Oct. 16, 2012   (FR) ...................... 12 59868

(51) Int. Cl.
*C07D 403/06*    (2006.01)
*C07D 207/333*   (2006.01)

(52) U.S. Cl.
CPC ......... *C07D 403/06* (2013.01); *C07D 207/333* (2013.01)

(58) Field of Classification Search
CPC .................................................. C07D 403/06
See application file for complete search history.

(56) References Cited

U.S. PATENT DOCUMENTS 6,635,656 B1 * 10/2003  Kashman ............. C07D 401/14
514/314

FOREIGN PATENT DOCUMENTS

| WO | WO 00/20411   | 4/2000 |
| WO | WO 2008/064317 | 5/2008 |

OTHER PUBLICATIONS

Chan et al. Cell Death and Disease, 2012, 3, e411.*
Luo et al. Cell 2009, 136, 823-837.*
Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) p. 427.*
Kamb, Nature Reviews Drug Discovery 4, 161-165 (Feb. 2005).*
Baldwin et al., *Total synthesis of cytotoxic sponge alkaloids Motuporamines A and B*, 40 Tetrahedron Letters 5401-5404 (1999).
Borgulya et al., *104. Catechol-O-methyltransferase-Inhibiting Pyrocatechol Derivatives: Synthesis and Structure—Activity Studies*, 72 Helvetica Chimica Acta 952-968 (1989).
Koren-Goldshlager et al., *Haliclorensin, a Novel Diamino Alkaloid from the Marine Sponge Haliclona tulearensis*, 61 J. Nat. Prod. 282-284 (1998).
Kashman et al., *Halitulin, A New Cytotoxic Alkaloid From the Marine Sponge Haliclona tulearensis*, 40 Tetrahedron Letters 997-1000 (1999).

(Continued)

*Primary Examiner* — Matthew Coughlin
(74) *Attorney, Agent, or Firm* — Buchanan Ingersoll & Rooney PC (57) ABSTRACT

The present invention relates to a compound of formula (I) in which: -m is an integer from 0 to 3, preferably from 0 to 2; n is an integer from 0 to 3, preferably from 0 to 2; $m+n \geq 1$; EAG is an electro-attractive group chosen independently from among a halogen atom, an $NO_2$, $CF_3$, $CCl_3$, CN, $CO_2H$, (C=O)$NR_2$, CH=NR, (C=S)OR, (C=O)SR, $CS_2R$, $SO_2R$, $SO_2NR_2$, $SO_3R$, $P(O)(OR)_2$, $P(O)(R)_2$, $B(OR)_2$ group where R is a ($C_1$-$C_6$) alkyl radical, a phenyl group or a hydrogen atom; A is a saturated or unsaturated, linear or branched hydrocarbon chain including 1 to 10 atoms of carbon; and $R_1$ and $R_2$ each represent independently from one another a hydrogen atom, a CO-(Ci-C6)-alkyl, ($C_1$-$C_6$) alkyl, phenyl or phenyl-($C_1$-$C_6$)-alkyl group, in which $R_1$ and $R_2$ form, together with the nitrogen atom they carry, a 5- to 15-member heterocycle, optionally substituted by a ($C_1$-$C_6$) alkyl group; including its stereoisomers and the mixtures thereof, or a pharmaceutically acceptable salt of same.

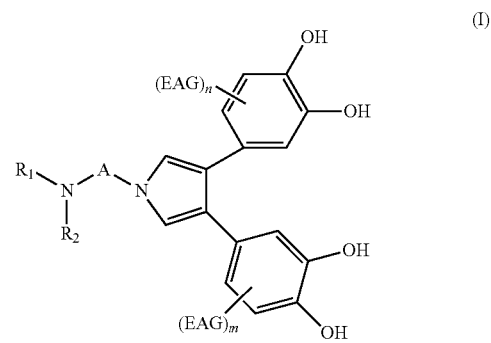

19 Claims, 9 Drawing Sheets

(56) References Cited

OTHER PUBLICATIONS

Kiss et al., *Discovery of a Long-Acting, Peripherally Selective Inhibitor of Catechol-O-methyltransferase*, 53 J. Med. Chem. 3396-3411 (2010).

Levin et al., *Derivatives of Dihydroeugenol and Certain Pharmacological Properties of Some of the Compounds*, 55 Derivatives of Dihydroeugenol 1995-2000 (May 1933).

Lu et al., *Synthesis and biological evaluations of novel apocynin analogues*, 46 European Journal of Medicinal Chemistry 2691-2698 (2011).

Wetson et al., *Tandem Conjugate Additions and 3-Aza-Cope Rearrangements of Tertiary Allyl Amines and Cyclic α-Vinylamines with Acetylenic Sulfones. Applications to Simple and Iterative Ring Expansions Leading to Medium and Large-Ring Nitrogen Heterocycles*, 73 J. Org. Chem. 4630-4637 (2008).

Williams et al., *Motuporamines, Anti-Invasion and Anti-Angiogenic Alkaloids from the Marine Sponge Xestospongia exigua (Kirkpatrick): Isolation, Structure Elucidation, Analogue, Synthesis, and Conformational Analysis*, 67 J. Org. Chem. 245-258 (2002).

French Search Report mailed on Jan. 14, 2013, in corresponding French Patent Application 772198.

International Search Report mailed on Nov. 19, 2013, corresponding PCT Application PCT/EP2013/071445.

\* cited by examiner

FIGURE 1

|       | 24hrs | 48hrs | 72hrs |
|-------|-------|-------|-------|
| 10nM  | -12%  | -18%  | -20%  |
| 25nM  | -40%  | -62%  | -50%  |
| 50nM  | -44%  | -83%  | -91%  |
| 100nM | -44%  | -83%  | -92%  |
| 200nM | -45%  | -86%  | -94%  |

Figure 2A:
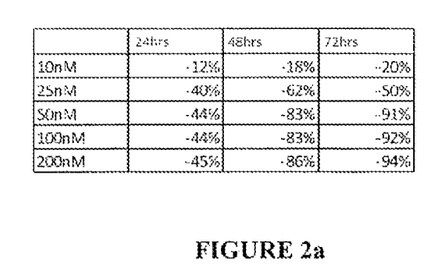

FIGURE 2a

|       | 24hrs | 48hrs | 72hrs |
|-------|-------|-------|-------|
|       | % viability | % viability | % viability |
| C     | 98 | 99 | 99 |
| 10nM  | 98 | 99 | 99 |
| 25nM  | 98 | 98 | 99 |
| 50nM  | 97 | 96 | 95 |
| 100nM | 97 | 97 | 98 |
| 200nM | 98 | 94 | 95 |

N-SUBSTITUTED 3,4-BIS (CATECHOL) PYRROLE COMPOUNDS, AND THE PREPARATION AND USE THEREOF IN THE TREATMENT OF CANCER

CROSS-REFERENCE TO RELATED APPLICATIONS

This application is a U.S. National Stage Application pursuant to 35 U.S.C. §371 of International Patent Application PCT/EP2013/071445, filed on Oct. 14, 2013, and published as WO 2014/060366 on Apr. 24, 2014, which claims priority to European Patent Application 1259868, filed on Oct. 16, 2012.

The present invention relates to novel N-substituted 3,4-bis(catechol) pyrrole compounds, the preparation and use thereof in the treatment of cancer.

Tumour cells originate from innate or acquired chromosomal modifications resulting from translocation, genic amplification, retroviral insertion, mutation, genetic deletion, and epigenetic disorders. These anomalies affect numerous genes involved in controlling the cell cycle, apoptosis, growth and survival, and DNA repair and stabilisation and detoxification genes.

The large majority of conventional anticancer chemotherapy is essentially based on the use of drugs wherein the mode of action involves blocking cell multiplication, either in the S phase of the cell cycle by attacking cell DNA or in the G2/M phase by attacking the microtubules of the mitotic spindle required for cell division. Further anticancer agents are intended to trigger programmed cell death by apoptosis, by inducing oxidative stress. The drawback of these approaches is the relative non-specificity of the drugs which are unable to spare healthy cells. Multiple side-effects follow. More recently, novel therapeutic approaches have been developed no longer using a cytotoxic action, as the curing means, but rather the use of an impediment to slow down or stop tumour growth. This targeted chemotherapy targets the intimate mechanisms of cell proliferation by blocking cell multiplication, by inhibiting growth factor signal transmission pathways, or by inhibiting angiogenesis.

However, with these novel targeted anticancer treatments, new forms of chemoresistance have emerged. They differ from the known chemoresistance mechanisms essentially associated with drug expulsion membrane system expression: ABC (ATP-Binding Cassette) protein including the MDR1 (Multi Drug Resistance-1) system. In this case, cancer cells develop chemoresistance by stimulating the survival pathway, associated with pro-apoptotic pathway inhibition. This survival pathway is activated by tyrosine kinase activity receptors (EGFR, PDGFR, IGFR), themselves activated by growth factors. It consists of PI3K (Phosphatidyl inositol 3 OH kinase), PDK (phosphoinositide-dependent tyrosine kinase), Akt (serine/threonine protein kinase PKB), PTEN (phosphatase and tensin homologue deleted on chromosome 10), FOXO (forkhead box O), mTOR (mammalian target of rapamycin) proteins, associated with the Src and Ras oncogenes. As a general rule, the survival pathway has a protective effect against apoptosis and may induce autophagy.

The link between the survival pathway and cancerogenesis is now well established. Indeed, mutations in the genes coding for the survival pathway are present in more than 30% of cancers including 70% of breast cancers: activating mutations of the PIK3CA, PIK3CB, AKT1, AKT2 genes, loss of PTEN function, and overexpression of the src and Ras oncogenes, regulating this pathway.

As such, for some years, compounds inhibiting this survival pathway have been developed to effectively combat cancer cells, which, in association with other drugs, block growth factor signal transmission.

Recent clinical trials have revealed that inhibiting the survival pathway blocked tumorigenesis. As such, the use of survival pathway inhibitors as an anticancer treatment may be considered as a new weapon against cancer.

One of the primary objectives of anticancer drug pharmacology is thus ongoing research on novel drugs liable to display superior therapeutic efficacy, via specific molecular targets, associated with the absence of chemoresistance and the absence of toxicity on healthy cells.

These fundamental criteria have been adopted for the selection of a novel antitumour drug.

The present invention relates to novel N-substituted 3,4-bis(catechol) pyrrole compounds having the general formula (I) hereinafter, the preparation thereof and the antimitotic action thereof and the mode of action thereof with respect to cancer cells.

wherein:

m is an integer from 0 to 3, preferably from 0 to 2;

n is an integer from 0 to 3, preferably from 0 to 2;

m+n≥1

EAG is an electro-attractive group chosen independently from among a halogen atom, an $NO_2$, $CF_3$, $CCl_3$, CN, $CO_2H$, (C=O)$NR_2$, CH=NR, (C=S)OR, (C=O)SR, $CS_2R$, $SO_2R$, $SO_2NR_2$, $SO_3R$, P(O)(OR)$_2$, P(O)(R)$_2$, B(OR)$_2$ group, where R is an alkyl ($C_1$-$C_6$) radical, a phenyl group or a hydrogen atom;

A is a saturated or unsaturated, linear or branched hydrocarbon chain including 1 to 10 atoms of carbon; and $R_1$ and $R_2$ each represent, independently from one another, a hydrogen atom, a CO—($C_1$-$C_6$)-alkyl, ($C_1$-$C_6$) alkyl, phenyl or phenyl-($C_1$-$C_6$)-alkyl group, where $R_1$ and $R_2$ form, together with the nitrogen atom bearing same, a 5- to 15-member heterocycle, optionally substituted by a ($C_1$-$C_6$) alkyl group;

including the stereoisomers and the mixtures thereof, or a pharmaceutically acceptable acid salt thereof.

The present invention particularly relates to the compound having formula (Ia) and the use thereof as a cancer treatment drug.

In particular, the radicals $R_1$ and $R_2$ form, together with the nitrogen atom bearing same, a heterocycle which is saturated and does not comprise any other heteroatom than the nitrogen atom bearing $R_1$ and $R_2$. More particularly, $R_1$ and $R_2$ form, together with the nitrogen atom bearing same, a 10- to 15-member, preferably 13-member, heterocycle.

In particular, the chain A is a saturated linear hydrocarbon chain comprising 3 to 6 carbon atoms, preferably 3 carbon atoms.

The present invention particularly relates to the compound having formula (1) or a pharmaceutically acceptable acid salt thereof.

and the use thereof as a cancer treatment drug.

It should be noted that, in vitro, the compound (1), used at concentrations encompassing the IC50 thereof, does not exhibit any cytotoxicity with respect to normal human cells.

In particular, the preferred pharmaceutically acceptable acid salt of the general formula (I), more particularly the compound (Ia) and preferentially the compound (1), is a hydrochloride.

The present invention also applies to a pharmaceutical composition comprising at least one compound having general formula (I), more particularly the compound (Ia) and preferentially the compound (1), with at least one pharmaceutically acceptable excipient.

The present invention relates to the use of the compounds (I), more particularly (Ia) and (1), as a drug in the treatment of cancer, in particular lung, breast, liver, stomach, colon, rectal, oesophageal, laryngeal, nasopharyngeal, pancreatic, prostate, kidney, bladder, duodenal, endometrial, pleural, skin, testicular, ovarian, uterine, brain, bone, oral, ocular cancer, or haematopoietic cancers such as leukaemias, myeloid leukaemias, lymphomas, bone marrow cancer or tumours of neuroectodermal origin such as glioblastomas.

The invention also relates to a process for preparing a compound having formula (I), more particularly (Ia) and (1) comprising:
a) reaction between an amine having the following formula (II), a halide having the following formula (III), and an aldehyde having the following formula (IV), wherein n and m, EAG, $R_1$, $R_2$ and A are as defined above with respect to the general formula (I), and X represents a halogen atom, to arrive at a compound having formula (I).
b) optionally, formation of a pharmaceutically acceptable salt from the compound having formula (I) obtained in the previous step a).

In this preparation process, the halide (III) and the amine (II) are first allowed to react with one another before adding the aldehyde (IV). Preferably, the radical X of the halide (III) is a chlorine, bromine or iodine atom.

Results

Chemical Synthesis

The compound 5,5'-(1-(3-(azacyclotridecan-1-yl)propyl)-1H-pyrrole-3,4-diyl)bis(3-nitrobenzene-1,2-diol) (1) was prepared by condensing the phenacyl halide 3 with the primary amine 2 and the phenylacetaldehyde 4, represented hereinafter:

N-(3-aminopropyl)azatricyclodecane (2) ((a) G. Koren-Goldshlager, Y. Kashman, M. Schleyer, J. Nat. Prod., 1998, 61, 282-284; (b) D. E. Williams, K. S. Craig, B. Patrick, L. M. McHardy, R. van Soest, M. Roberge, R. J. Andersen, J. Org. Chem., 2002, 67, 245-258) was obtained from commercial laurolactam as per diagram 1 hereinafter:

Diagram 1

Compounds 3 (J. Borgulya, H. Bruderer, K. Bernauer, G. Zürcher, M. Da Prada, Helv. Chim. Acta, 1989, 72, 952-968) and 4 were prepared as per diagram 2 hereinafter:

Diagram 2

A monotope formation method was developed for the synthesis of the pyrrole 5 from the amine 2, the halide 3 and the phenylacetaldehyde 4 (Diagram 3).

Diagram 3

26%

By treating compound 5 with a solution of BBr$_3$ in dichloromethane, the demethylated product (1) was obtained (Diagram 4).

Diagram 4

The corresponding hydrochloride was obtained by treating with a solution of HCl in methanol.

EXPERIMENTAL SECTION

Preparation of 3-(azacyclotridecan-1-yl)propan-1-amine (2)

Azacyclotridecane ((a) J. E. Baldwin, H. R. Vollmer, V. Lee, Tetrahedron Lett., 1999, 40, 5401-5404; (b) M. H. Weston, K. Nakajima, T. G. Back, J Org. Chem., 2008, 73, 4630-4637)

To a solution of azacyclotridecan-2-one (4.3 g; 21.8 mmol) in THF (100 ml) at AT in argon, LiAlH$_4$ (1.5 g; 39.5 mmol) is gradually added and the reaction mixture is heated to reflux for 16 hours. A saturated Na$_2$SO$_4$ solution is then gradually added at 0° C. to neutralise the excess LiAlH$_4$, a 1:1 ether/pentane mixture (200 ml) is then added along with excess solid K$_2$CO$_3$ to absorb the entire aqueous phase. The organic phase is then settled and the precipitate is washed three times with a 1:1 ether/pentane mixture. The solvent is removed at reduced pressure to arrive at azacyclotridecane (3.9 g; 98%) in colourless oil form.

$^1$H NMR (CDCl$_3$; 300 MHz) δ (ppm) 2.62 (4 H; t; J=5.1 Hz); 1.57-1.25 (20 H; m). $^{13}$C NMR (CDCl$_3$; 75 MHz) δ (ppm) 47.9; 27.9; 26.5; 26.0; 25.4; 24.6.

3-(Azacycltridecan-1-yl)propanenitrile

To a solution of azacyclotridecane (3.8 g; 20.7 mmol) and triethylamine (50 µl; 0.35 mmol) in DMF (15 ml) in argon, acrylonitrile (7.7 ml; 115 mmol) is added and the reaction mixture is stirred for 16 hours at 70° C. The reaction mixture is extracted with ether, the organic phase is washed with brine, dried on Na$_2$SO$_4$, and evaporated at reduced pressure to arrive at 3-(azacyclotridecan-1-yl)propanenitrile in colourless oil form (4.64 g; 95%). $^1$H NMR (CDCl$_3$; 300 MHz) δ (ppm) 2.76 (2 H; t; J=7.2 Hz); 2.50-2.35 (6 H; m); 1.55-1.28 (20 H; m). $^{13}$C NMR (CDCl$_3$; 75 MHz) δ (ppm) 53.7; 49.7; 26.5; 26.2; 25.23; 25.18; 15.7.

3-(Azacyclotridecan-1-yl)propan-1-amine (2) ((a) G. Koren-Goldshlager, Y. Kashman, M. Schleter, J. Nat. Prod., 1998, 61, 282-284; (b) D. E. Williams, K. S. Craig, B. Patrick, L. M. McHardy, R. van Soest, M. Roberge, R. J. Andersen, J. Org. Chem., 2002, 67, 245-258).

To a solution of 3-(azacyclotridecan-1-yl)propanenitrile (0.5 g; 2.1 mmol) in ether (15 ml) at 0° C. in argon, LiAlH$_4$ (0.3 g; 7.9 mmol) is gradually added and the reaction mixture is stirred at 33° C. for 15 min. A saturated Na$_2$SO$_4$ solution is then gradually added at 0° C. to neutralise the excess LiAlH$_4$, and solid K$_2$CO$_3$ is then added to absorb the entire aqueous phase. The organic phase is settled and the precipitate is washed three times with ether. The solvent is removed at reduced pressure to arrive at 2 (0.49 g, 96%) in colourless oil form. $^1$H NMR (CDCl$_3$; 500 MHz) δ (ppm) 2.74 (2 H; t; J=7.0 Hz); 2.40-2.28 (6 H; m); 1.57 (2 H; quint; J=7.0 Hz); 1.44-1.32 (22 H; m). $^{13}$C NMR (CDCl$_3$; 125 MHz) δ (ppm) 54.4; 52.8; 41.2; 31.7; 26.7; 26.5; 26.3; 25.8; 25.6.

Preparation of 2-bromo-1-(4-hydroxy-3-methoxy-5-nitrophenyl)ethanone (3)

1-(4-Hydroxy-3-methoxy-5-nitrophenyl)ethanone ((a) L. E. Kiss, H. S. Ferreira, L. Torrão, M. J. Bonifácio, P. N. Palma, P. Soares-da-Silva, D. A. Learnmonth, J. Med. Chem., 2010, 53, 3396-3411; (b) X. Lu, S. Wan, J. Jiang, X. Jiang, W. Yang, P. Yu, L. Xu, Z. Zhang, G. Zhang, L. Shan, Y. Wang, Eur. J. Med. Chem., 2011, 46, 2691-2698).

To a solution of 4'-hydroxy-3'-methoxyacetophenone (10 g; 60.2 mmol) in acetic acid (140 ml) at AT, 70% HNO$_3$ is added (4.2 ml; 66.3 mmol). The reaction mixture is stirred for 30 min and the yellow crystals are filtered, washed with ether and dried to arrive at 1-(4-Hydroxy-3-methoxy-5-nitrophenyl)ethanone (10.5 g; 83%), mp 158-159° C. (lit. 159-161° C., ethanol, X. Lu, S. Wan, J. Jiang, X. Jiang, W. Yang, P. Yu, L. Xu, Z. Zhang, G. Zhang, L. Shan, Y. Wang, Eur. J. Med. Chem., 2011, 46, 2691-2698). $^1$H NMR (CDCl$_3$; 300 MHz) δ (ppm) 11.09 (1 H; s), 8.30 (1 H; d; J=1.5 Hz); 7.75 (1 H; d; J=1.5 Hz); 4.01 (3 H; s); 2.62 (3 H; s). $^{13}$C NMR (CDCl$_3$; 75 MHz) δ (ppm) 194.9; 150.4; 150.1; 133.0; 128.3; 117.7; 115.3; 56.9; 26.0. IR (neat) v$_{max}$ cm$^{-1}$ 3228; 3091; 2988; 2925; 1676; 1612; 1535; 1413; 1378; 1350; 1329; 1218; 1136; 1047; 869; 735; 709; HRMS (DE) (m/z) [M–H]$^-$ calculated for C$_9$H$_8$NO$_5$ 210.0402; obtained 210.0404.

2-Bromo-1-(4-hydroxy-3-methoxy-5-nitrophenyl)ethanone (3) (J. Borgulya, H. Bruderer, K. Bernauer, G. Zürcher, M. Da Prada, Helv. Chim. Acta, 1989, 72, 952-968).

To a solution of 1-(4-hydroxy-3-methoxy-5-nitrophenyl)ethanone (9.6 g; 45.5 mmol) in CH$_2$Cl$_2$ (200 ml) at AT, bromine (2.4 ml; 46.8 mmol) is gradually added and the reaction mixture is stirred for 10 min. During this period, the colour of the bromine disappears completely. Pentane (400 ml) is then added. After 10 min, the yellow crystals are filtered under a hood, washed with a 1:1 pentane/ether mixture, and dried to arrive at 3 (10 g; 76%), mp 143-145° C. (lit. 147-149° C.; J. Borgulya, H. Bruderer, K. Bernauer, G. Zürcher, M. Da Prada, Helv. Chim. Acta, 1989, 72, 952-968). $^1$H NMR (CDCl$_3$; 300 MHz) δ (ppm) 11.18 (1 H; s), 8.36 (1 H; d; J=1.8 Hz); 7.77 (1 H; d; J=1.8 Hz); 4.44 (2 H; s); 4.03 (3 H; s). $^{13}$C NMR (CDCl$_3$; 75 MHz) δ (ppm) 188.7; 150.7; 150.6; 133.0; 125.0; 118.3; 115.9; 57.0; 29.4. IR (neat) v$_{max}$ cm$^{-1}$ 3366; 3093; 2991; 2942; 1765; 1689; 1608; 1535; 1386; 1246; 1151; 1060; 912; 887; 850; 762. HRMS (DE) (m/z) [M–H]$^-$ calculated for C$_9$H$_7$$^{79}$BrNO$_5$ 287.9508; obtained 287.9480.

Preparation of 2-(4-hydroxy-3-methoxy-5-nitrophenyl)acetaldehyde (4)

4-Allyl-2-methoxy-6-nitrophenol (D. E. Lewin, A. Lowy, J. Am. Chem. Soc., 1933, 55, 1995-2000).

To a solution of eugenol (6.76 g; 41.2 mmol) in acetic acid (100 ml) at AT, 70% HNO$_3$ is added (2.8 ml; 44.2 mmol). The reaction mixture is stirred for 15 min, extracted with ether, washed vigorously with brine, and finally with a phosphate buffer (pH=7). The ether solution is diluted with the same volume of pentane, filtered on silica gel and evaporated under reduced pressure to arrive at 4-allyl-2-methoxy-6-nitrophenol (6.36 g, 79%) in the form of dark red oil. $^1$H NMR (CDCl$_3$; 300 MHz) δ (ppm) 10.61 (1 H; sl), 7.48 (1 H; d; J=1.5 Hz); 6.96 (1 H; d; J=1.5 Hz); 5.91 (1 H; m); 5.20-5.08 (2 H; m); 3.92 (3 H; s); 3.35 (2 H; d; J=6.6 Hz). $^{13}$C NMR (CDCl$_3$; 75 MHz) δ (ppm) 149.8; 144.8; 135.9; 133.6; 131.2; 118.6; 117.1; 115.0; 56.7; 39.4. IR (neat) v$_{max}$ cm$^{-1}$ 3225; 3080; 2976; 2939; 1639; 1539; 1428; 1390; 1326; 1259; 1133; 1061; 916; 763. HRMS (DE) (m/z) [M+Na]$^+$ calculated for C$_{10}$H$_{11}$NNaO$_4$ 232.0586; obtained 232.0578.

2-(4-Hydroxy-3-methoxy-5-nitrophenyl)acetaladehyde (4)

To a solution of 4-allyl-2-methoxy-6-nitrophenol (2.0 g; 9.6 mmol) in THF (23 ml) and water (8 ml) at 0° C., a 0.166

M osmium tetroxide solution (23 mg/0.09 mmol) in a 7:5 THF/water mixture (0.55 ml) is added. After 5 min, NaIO$_4$ (4.8 g; 22 mmol) is added. The reaction mixture is stirred for 1 hour at 0° C., allowed to return gradually to AT for 1 hour, extracted with a 1:1 CH$_2$Cl$_2$/ether mixture and the organic phase is washed once with brine, dried on Na$_2$SO$_4$, and evaporated at reduced pressure at 25° C. The residue is dissolved in the minimum volume of CH$_2$Cl$_2$ and a 1:1 pentane/ether mixture is added. The solvent is evaporated at reduced pressure at 25° C. until yellow crystals are formed; pentane is added and the solution is concentrated once again. The crystals are filtered to arrive at 4 (1.66 g, 82%), mp 130-132° C. $^1$H NMR (CDCl$_3$; 300 MHz) δ (ppm) 10.71 (1 H; s), 9.80 (1 H; t; J=1.8 Hz); 7.57 (1 H; d; J=1.8 Hz), 6.97 (1 H; d; J=1.8 Hz), 3.96 (3H; s); 3.74 (2H; d; J=1.8 Hz).

$^{13}$C NMR (CDCl$_3$; 75 MHz) δ (ppm) 197.8; 150.4; 145.8; 133.8; 123.1; 119.0; 116.6; 56.8; 49.5. IR (neat) $v_{max}$ cm$^{-1}$ 3226; 1720; 1583; 1449; 1333; 1264; 1238; 1134; 1064; 921; 764. HRMS (DE) (m/z) [M–H]$^-$ calculated for C$_9$H$_8$NO$_5$ 210.0402; obtained 210.0399.

5-(1-(3-(Azacyclotridecan-1-yl)propyl)-4-(4-hydroxy-3-methoxy-5-nitrophenyl)1-H-pyrrol-3-yl)-3-nitrobenzene-1,2-diol (5)

Phenacyl bromide 3 (1.23 g; 4.2 mmol) and NaI (3.2 g; 21 mmol) are added to a solution of amine 2 (1 g, 4.2 mmol) in DMSO (20 ml) at AT in argon and the reaction mixture is stirred for 15 min at AT. A solution of aldehyde 4 (900 mg, 4.3 mmol) in methanol (60 ml) is then added and the reaction mixture is stirred for 16 hours at AT. It is extracted with CH$_2$Cl$_2$ and the organic phase is washed with a saturated NaHCO$_3$ solution, brine, dried on Na$_2$SO$_4$, evaporated at reduced pressure and silica gel chromatography (elution gradient of CH$_2$Cl$_2$ with 80:1 CH$_2$Cl$_2$/MeOH) to arrive at 5 (682 mg, 26%) in the form of an amorphous red solid. $^1$H NMR (CDCl$_3$; 500 MHz) δ (ppm) 7.65 (2 H; d; J=2.0 Hz); 7.01 (2 H; d; J=2.0 Hz); 6.87 (2 H; s); 4.05 (2 H; t; J=7.0 Hz); 3.77 (6 H; s); 2.70-2.43 (6 H; m); 2.15 (2 H; quint; J=7.5 Hz); 1.66-1.34 (20 H; m). $^{13}$C NMR (CDCl$_3$; 75 MHz) δ (ppm) 149.7; 144.8; 133.9; 126.7; 121.0; 120.7; 118.7; 114.5; 56.8; 53.0; 51.7; 47.7; 27.9; 25.7; 25.6; 25.5; 25.2; 23.9. IR (neat) $v_{max}$ cm$^{-1}$ 3255; 2930; 2859; 1552; 1522; 1464; 1337; 1240; 1156; 919; 732. HRMS (DE) (m/z) [M+H]$^+$ calculated for C$_{33}$H$_{45}$N$_4$O$_8$ 625.3237; obtained 625.3228.

5,5'-(1-(3-(Azacyclotridecan-1-yl)propyl)-1H-pyrrole-3,4-diyl)bis(3-nitrobenzene-1,2-diol) (1)

To compound 5 (50 mg; 0.080 mmol) in argon at AT, BBr$_3$ (1M solution in CH$_2$Cl$_2$, 2 ml; 2 mmol). The heterogeneous mixture is stirred for 30 min at AT. A 1:1 CH$_2$Cl$_2$/pentane mixture (30 ml) is added and, after 5 min, the precipitate is separated, washed with the same solvent mixture and dissolved in the minimum volume of 10:1 CH$_2$Cl$_2$/ethanol. The solution is introduced onto a silica gel column, eluted with 20:1 CH$_2$Cl$_2$/ethanol and evaporated at reduced pressure to arrive at 1 in the form of red-orange amorphous solid (44 mg; 92%). $^1$H NMR (CD$_3$OD; 300 MHz) δ (ppm) 7.44 (2 H; d; J=1.8 Hz); 7.00 (2 H; s); 6.97 (2 H; d; J=1.8 Hz); 4.12 (2 H; t; J=6.3 Hz); 3.30-3.12 (6 H; m); 2.32 (2 H; quint; J=6.0 Hz); 1.85-1.70 (4 H; m); 1.60-1.39 (16 H; m). $^{13}$C NMR (CD$_3$OD; 75 MHz) δ (ppm) 147.5; 141.9; 134.7; 127.0; 121.4; 121.3; 120.5; 113.5; 52.4; 52.0; 46.1; 25.9; 25.3; 24.6; 24.2; 23.9; 21.2. IR (neat) $v_{max}$ cm$^{-1}$ 3379; 2932; 1621; 1555; 1471; 1300; 1236; 803; 762; 667. HRMS (DE) (m/z) [M+H]$^+$ calculated for C$_{31}$H$_{41}$N$_4$O$_8$ 597.2924; obtained 597.2938.

Hydrochloride 1.HCl

To a solution of 1 in a minimum volume of dichloromethane, a solution of 2 M HCl in methanol (5 equiv) diluted in ether is added. The precipitate formed is then filtered and dried. MP 179-184° C. (settled). $^1$H NMR (DMSO-d$_6$; 300 MHz) δ (ppm) 7.19 (2 H; d; J=3.0 Hz); 7.06 (2 H; s); 6.90 (2 H; d; J=3.0 Hz); 4.00 (2 H; t; J=6.0 Hz); 3.15-2.97 (6 H; m); 2.24 (2 H; quint; J=6.0 Hz); 1.75-1.58 (4 H; m); 1.44-1.28 (16 H; m). $^{13}$C NMR (DMSO-d$_6$; 75 MHz) δ (ppm) 148.0; 140.4; 137.7; 126.7; 121.3; 120.5; 120.1; 113.5; 51.9; 51.2; 46.7; 25.9; 25.7; 24.9; 24.7; 24.4; 20.9. IR (neat) $v_{max}$ cm$^{-1}$ 3111; 2930; 2861; 1552; 1463; 1293; 1233;

1061; 866; 801; 762. HRMS (DE) (m/z) [M-HCl-H]⁻ calculated for $C_{31}H_{39}N_4O_8$ 595.2768; obtained 595.2773.

In Vitro Biological Study

The biological activity of compound (1) was studied in vitro on 3 different cancer cell lines:
- HCT-116 (colorectal carcinoma)
- U87 (glioblastoma)
- K562 (myeloid leukaemia)

and on 3 normal non-cancerous cell types:
- HUVEC (human umbilical vascular endothelial cells)
- NHDF (human dermal fibroblasts)
- HFDPC (human hair follicle dermal papilla cells).

The cells selected for this study were incubated at 37° in the presence of compound (1) added in the culture medium at different concentrations and at different times.

The set of experiments conducted made it possible to determine the degree of toxicity of the compound under test, study the effect thereof on the progression of the cell cycle and the capability thereof of inducing an autophagic response and cell death by apoptosis. We studied the mode of action thereof in order to determine the molecular target thereof.

1. Study of the Effect of Compound (1) on Cell Growth

Figure 1:
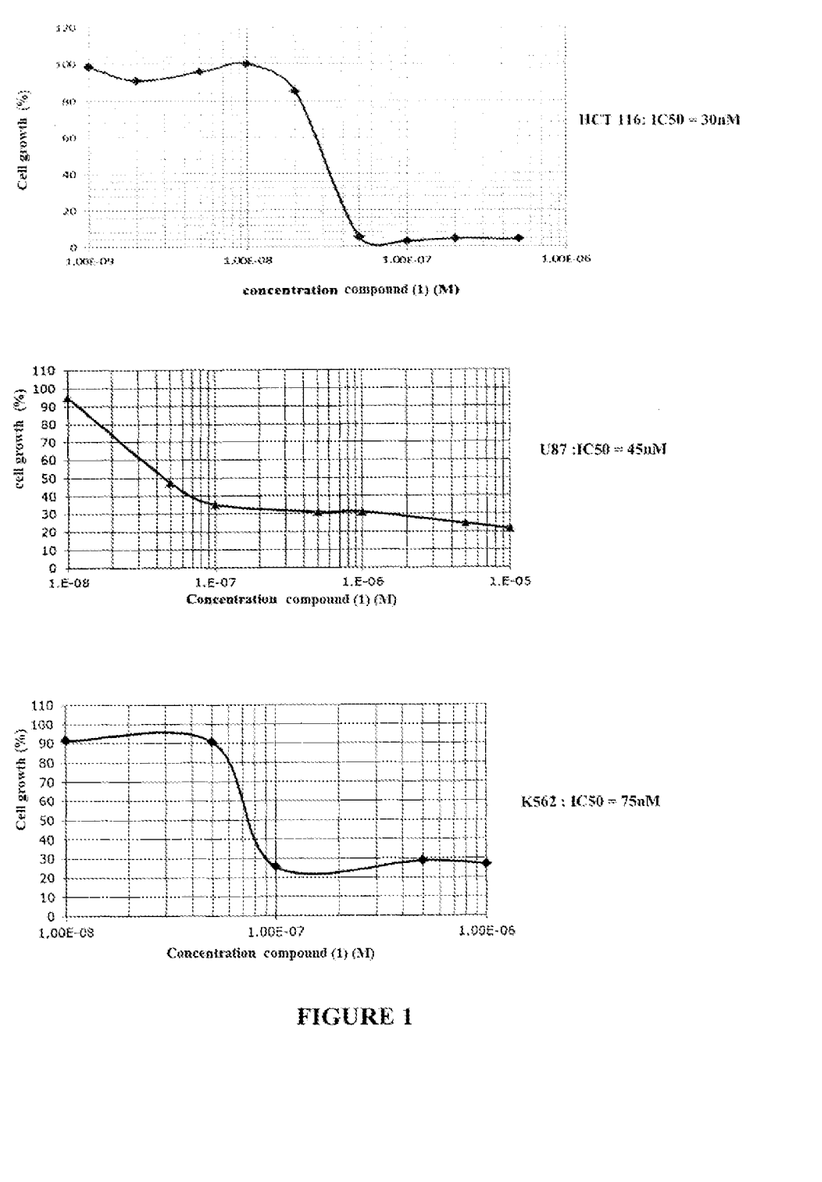

The effect of compound (1) on HCT-116, U87 and K562 cell growth was evaluated using a cell growth test (CellTiter-Blue™ m Cell Viability Assay, Promega). The growth curves and the IC50 values (concentration of compound inducing a 50% reduction of cell growth) determined after 72 hours of cell treatment with compound (1) are presented in FIG. 1. They are 30 nm for HCT-116 cells, 45 nM for U87 cells and 70 nM for K562.

The effect of compound (1) on cell growth was described in more detail on the HCT-116 cell line. This study was conducted as a function of the concentration and exposure time of the cells to the molecule under test (24 hrs, 48 hrs and 72 hrs) by counting the number of live cells after excluding dead cells by means of trypan blue staining.

FIG. 2 represents the effect of compound (I) on the number and viability of HCT-116 cells as a function of the concentration thereof and the treatment time.

Figure 2B:
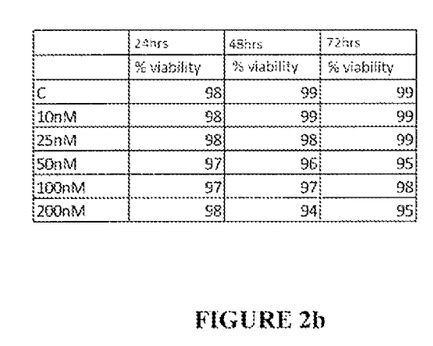

The results presented in FIG. 2a demonstrate that the number of cells decreases as a function of the concentration thereof and the treatment time with compound (1). Compound (1) at the 25 nM concentration already exhibits an activity from 24 hours of treatment by reducing the number of cells by 40%, reaching up to 80% inhibition from 48 hours for concentrations greater than the IC50. This inhibitory effect is however associated with a lack of modification of cell viability (FIG. 2b). This indicates that the action of compound (1) is cytostatic and not cytotoxic.

Figure 3:
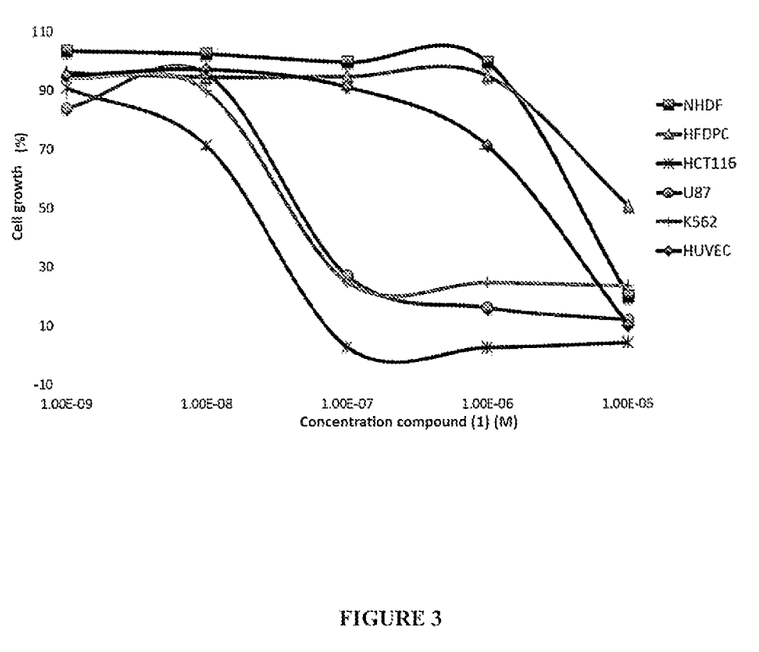

In order to determine the specificity of action of compound (1) on cancer cells, we evaluated the effect thereof with respect to normal human HUVEC, NHDF and HFDPC cells and the HCT-116, U87 and K652 cancer cell annotations. The results presented in FIG. 3 demonstrated that the IC50 determined after 72 hours of treatment with compound (1) is 2 μm for HUVEC cells, 5 μM for NHDF cells and 10 μM for HFDPC.

The IC50 values are thus up to 300 times higher for normal cells compared to those obtained for cancer cells. This clearly indicates that malignant cells are significantly more sensitive to the action of compound (1) compared to healthy cells.

2. Study of the Effect of Compound (1) on the Cell Cycle

Figure 4:
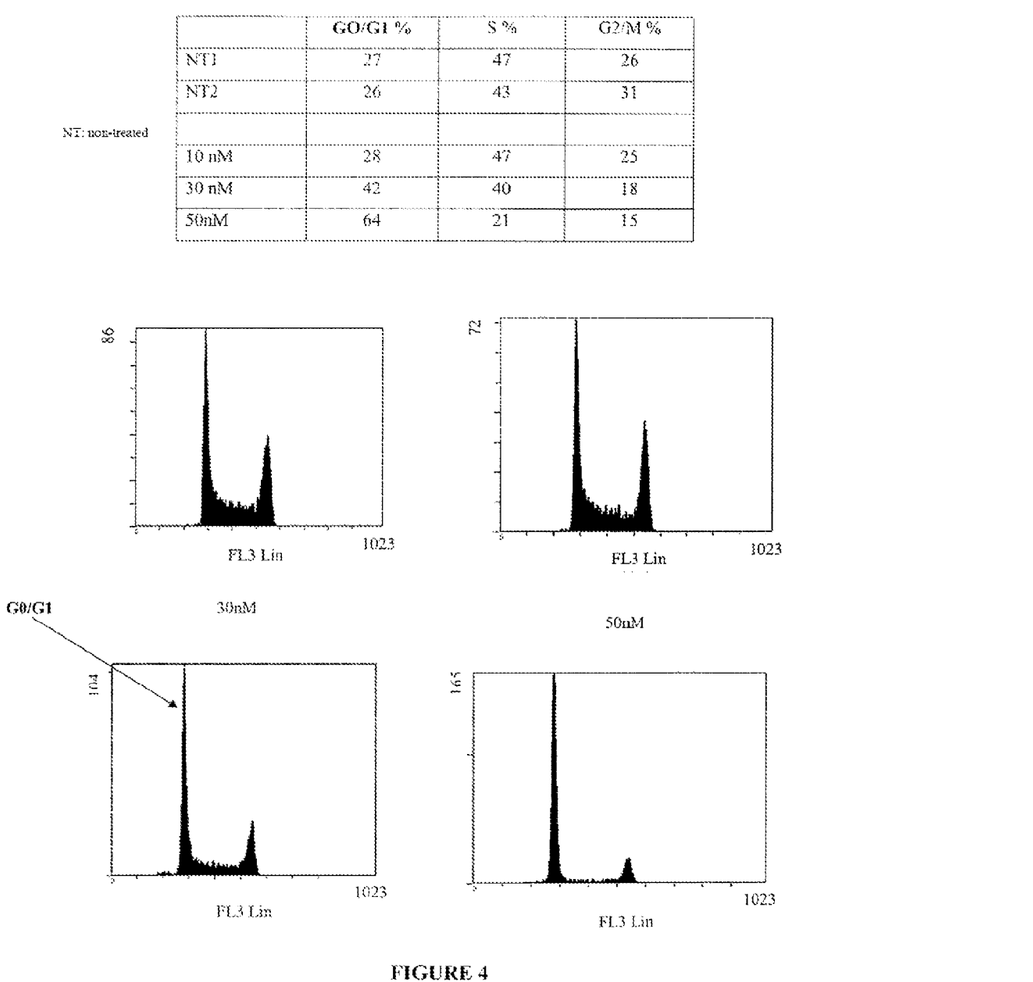

The flow cytometry analysis (FC500, Beckman Coulter) of HCT-116 cells treated with compound (1) demonstrated that this compound blocks cell division in the G0/G1 phase. This effect is significant after 24 hours of exposure of the cells to compound (1) used at the 30 and 50 nM concentrations (FIG. 4).

Figure 5:
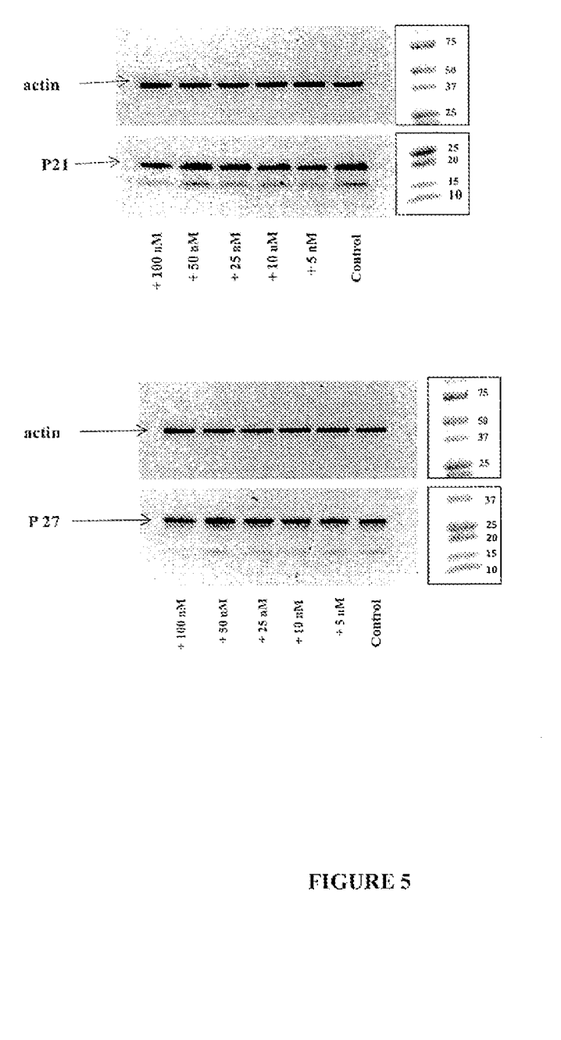

3. Study of the Effect of Compound (1) on the Expression of the Proteins p21 and p27 Involved in Stopping the Cell Cycle On the basis of the above results demonstrating a stoppage of the cycle in G0/G1, associated with a reduction in the number of cells in the absence of toxicity, we evaluated the expression of the proteins p21 and p27 associated with stopping the cell cycle in G0/G1. The gene of the protein p27 is described as being regulated by FOXO3, whereas that of the protein p21 is controlled by the p53 transcription factor, stimulated inter alia by oxidative stress. The HCT-116 cells were treated with compound (1) for 24 hours. The cell extracts were then analysed by Western Blot. The results presented in FIG. 5 demonstrate an increase in the expression of protein p27 following the treatment with compound (1) at the 25 and 50 nM concentrations. Compound (1) has no significant effect on the expression of the protein p21.

4. Study of the Effect of Compound (1) on Apoptosis Induction

In order to maintain that compound (1) does not induce cell death by apoptosis, the HCT-116 cells treated for 24 hours were analysed to evaluate the activity of caspases 3 and 7 and the modification of mitochondrial transmembrane potential.

Figure 6A:
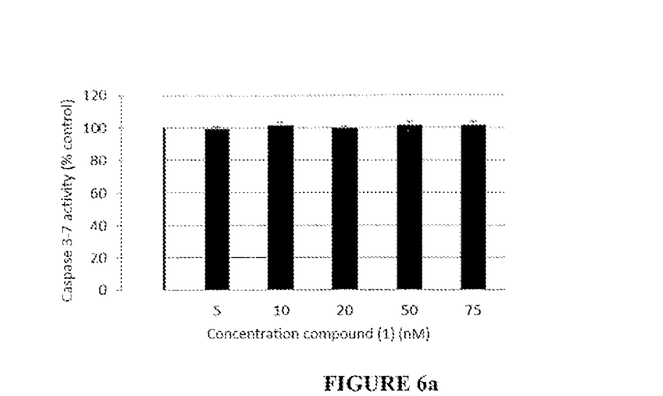

The activity of caspases 3 and 7, marker enzymes of apoptosis, was measured using the Apo-ONE (Promega) test after treating HCT-116 cells with compound (1) at concentrations varying from 5 nM to 75 nM. The results presented in FIG. 6a demonstrate the lack of variations in the activity of these enzymes following the treatment with the molecule under test.

The study of the mitochondrial transmembrane potential, Δψm, was conducted by flow cytometry, using the JC-1 probe (MitoProbe™ JC-1 assay, Molecular Probes). JC-1 is a lipophilic anionic compound which selectively penetrates the mitochondria, the colour whereof changes from green to red when the transmembrane potential increases. Unlike healthy cells, cells in apoptosis exhibit a low Δψm which is associated with a strong green colour of the JC-1 probe.

Figure 6B:
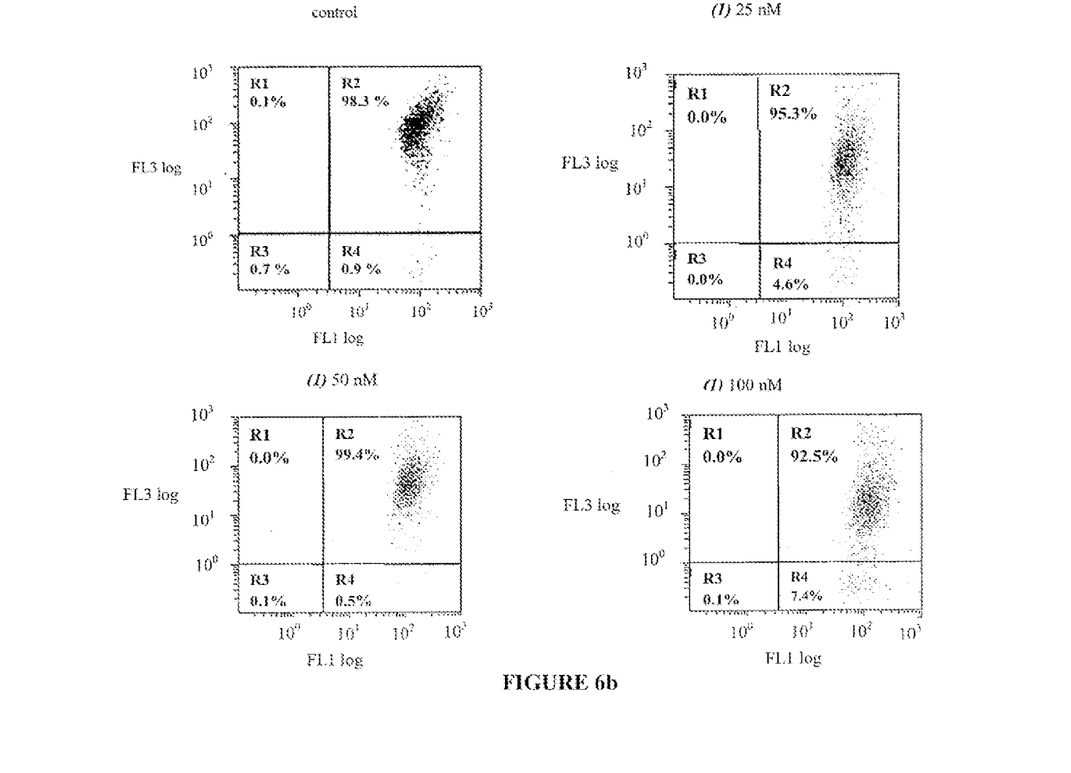

The results presented in FIG. 6b demonstrate that treating HCT-116 cells with compound (1) at concentrations varying from 25 nM to 100 nM does not modify Δψm significantly. All these results indicate that compound (I) does not induce the caspase-dependent apoptotic pathway (type I programmed cell death).

5. Study of Autophagy

In the aim of determining whether the stoppage of the cell cycle induced by compound (1) induces an autophagic reaction, the HCT-116 cells were treated with compound (1) at different doses for 24 hours. The cell extracts then underwent Western Blot analysis in order to view the expression of the protein LC3-II. Indeed, the protein LC3 exists in the cell either in cytosolic form (LC3-I) or associated with phagosomes (LC3-II). The latter is the marker of the autophagic reaction.

Figure 7:
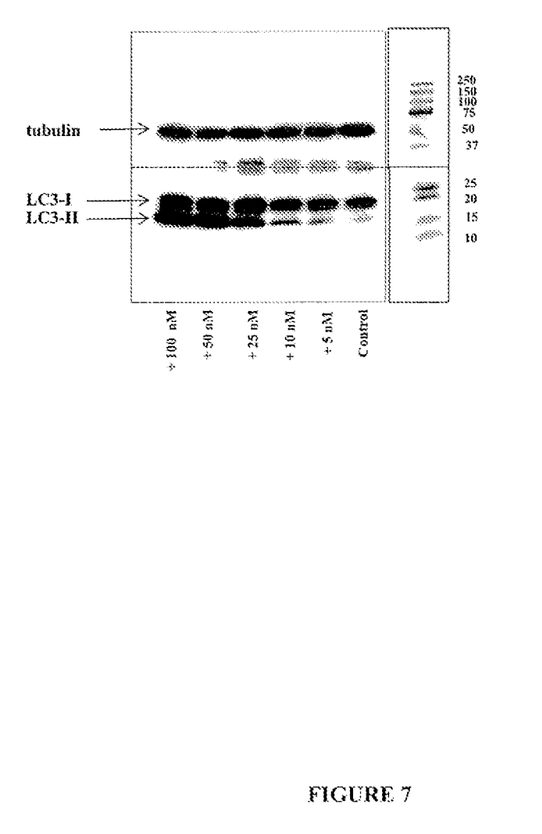

The results presented in FIG. 7 clearly show an increase in the expression of LC3-II in the presence of compound (1) used at concentrations varying from 5 nM to 100 nm.

6. Study of the Mode of Action of Compound (1)

In view of the stoppage of the cell cycle in the G0/G1 phase associated with an autophagic response in the absence of apoptosis following treatment with compound (1), we studied the action of this compound on the survival pathway involving PI3 kinase-Akt-Foxo. This signalling pathway is very frequently found to be disrupted (by stimulation) in a large number of cancer cells and contributes to the survival thereof.

Figure 8A:
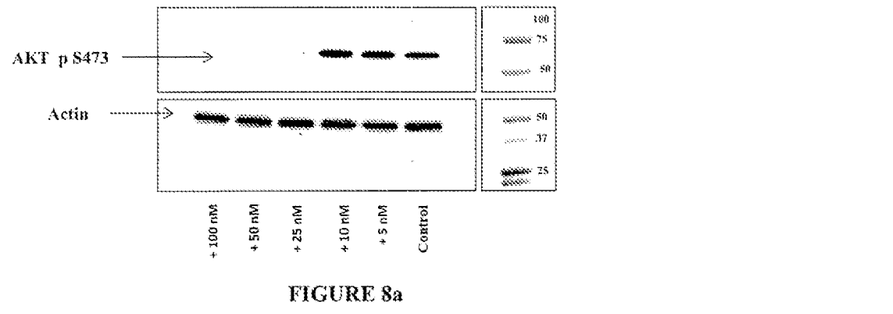
Figure 8B:
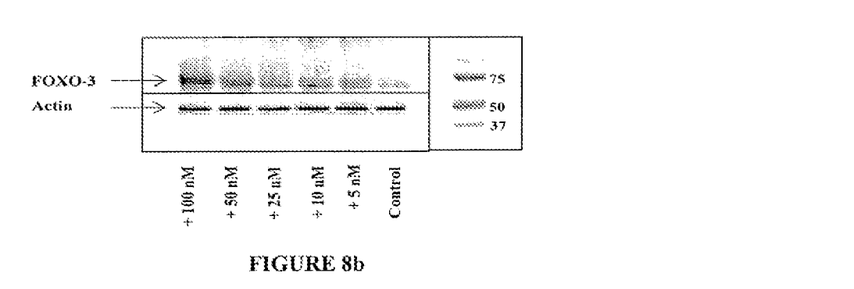
Figure 8C:
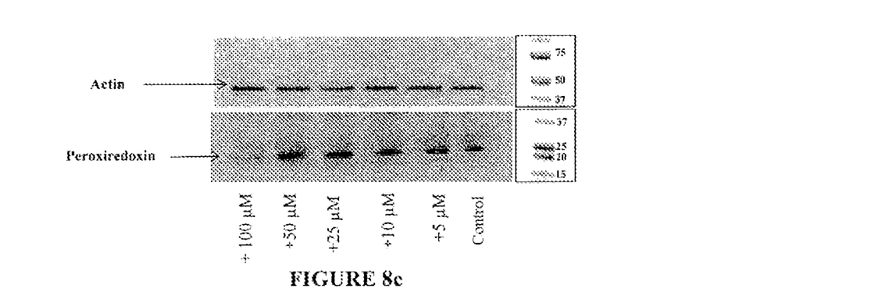

The results presented in FIG. 8 demonstrate that compound (1) blocks this survival pathway. Indeed, HCT-116 cells were exposed for 24 hours to the action of compound (1) at concentrations varying from 5 nM to 100 nm. The Western Blot analysis of the cell extracts revealed that compound (1), from the 25 nm concentration, totally suppresses Akt protein serine 473 phosphorylation (FIG. 8a). It stimulates the expression of the protein FOXO3 (FIG. 8b), the synthesis whereof is reduced by the Akt-phosphorylated protein. It stimulates the expression of the protein peroxiredoxin 1, the gene whereof is described as being under the control of the FOXO3 factor (FIG. 8c).

Figure 9A:
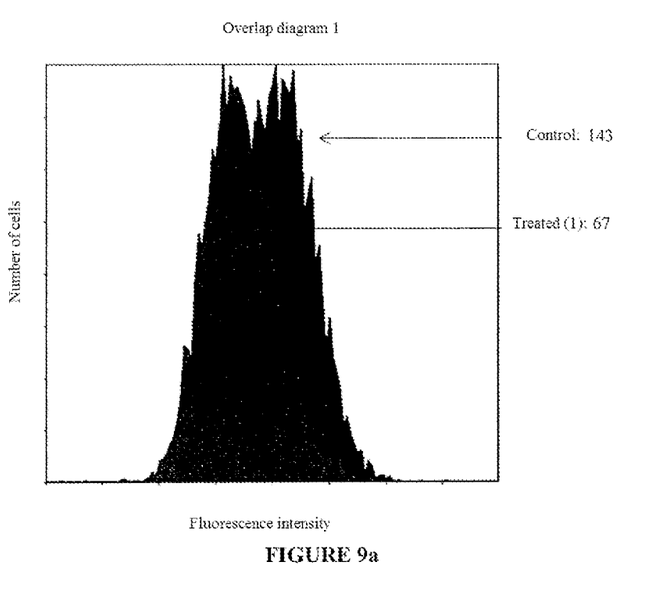
Figure 9B:
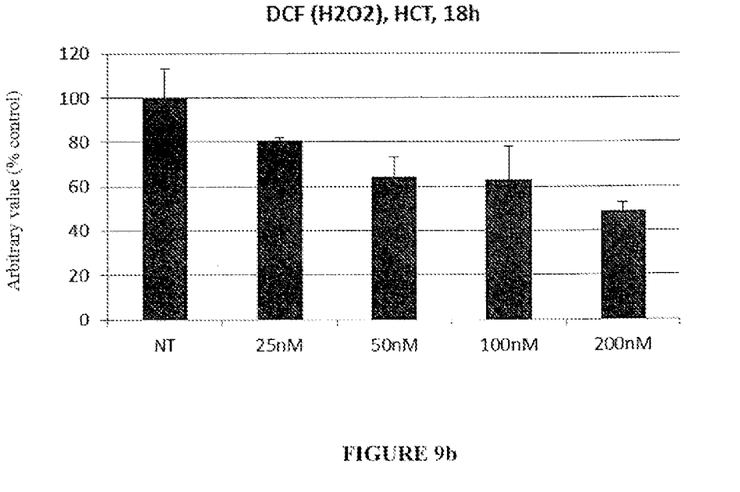

The protein peroxiredoxin is an enzyme having a peroxidase activity, controlling the intracellular hydrogen peroxide ($H_2O_2$) concentration. Therefore, we evaluated the effect of compound (1) on the intracellular $H_2O_2$ concentration, using DCF-DA (2',7'-dichlorofluorescein diacetate, Sigma) as a marker of intracellular $H_2O_2$. Hydrogen peroxide is an intracellular second messenger. It regulates, according to the concentration thereof, numerous functions such as proliferation or apoptosis. A reduction of the concentration thereof is associated with a decrease in proliferation. The flow cytometry analysis results of HCT-116 cells treated with compound (1) at the 50 nM concentration demonstrate a decrease by approximately 50% of the intracellular $H_2O_2$ concentration after 18 hours of treatment (FIG. 9a). The effect observed is dose dependent (FIG. 9b).

The invention claimed is:
1. A compound having the following formula (I):

wherein:
m is an integer from 0 to 3;
n is an integer from 0 to 3;
m+n≥1
EAG is an electro-attractive group chosen independently from among a halogen atom, an $NO_2$, $CF_3$, $CCl_3$, CN, $CO_2H$, (C=O)$NR_2$, CH=NR, (C=S)OR, (C=O)SR, $CS_2R$, $SO_2R$, $SO_2NR_2$, $SO_3R$, $P(O)(OR)_2$, $P(O)(R)_2$, $B(OR)_2$ group, where R is an alkyl ($C_1$-$C_6$) radical, a phenyl group or a hydrogen atom;
A is a saturated or unsaturated, linear or branched hydrocarbon chain including 1 to 10 atoms of carbon; and
$R_1$ and $R_2$ each represent, independently from one another, a hydrogen atom, a CO—($C_1$-$C_6$)-alkyl, ($C_1$-$C_6$) alkyl, phenyl or phenyl-($C_1$-$C_6$)-alkyl group, or $R_1$ and $R_2$ form, together with the nitrogen atom bearing same, a 5- to 15-member heterocycle, optionally substituted by a ($C_1$-$C_6$) alkyl group;

including the stereoisomers and the mixtures thereof, or a pharmaceutically acceptable acid salt thereof.

2. The compound according to claim 1, having the following formula (Ia):

wherein the radicals $R_1$ and $R_2$ have the meanings given in claim 1, including the stereoisomers and the mixtures thereof, or a pharmaceutically acceptable acid salt thereof.

3. The compound according to claim 1, wherein the radicals $R_1$ and $R_2$ form, together with the nitrogen atom bearing same, a heterocycle which is saturated and does not comprise any other heteroatom than the nitrogen atom bearing $R_1$ and $R_2$.

4. The compound according to claim 1, wherein the radicals $R_1$ and $R_2$ form, together with the nitrogen atom bearing same, a 10- to 15-member heterocycle.

5. The compound according to claim 1, wherein A is a saturated linear hydrocarbon chain comprising 3 to 6 carbon atoms.

6. The compound according to claim 1, corresponding to the compound having the following formula (1):

or a pharmaceutically acceptable acid salt thereof.

7. The compound according to claim 1, wherein the pharmaceutically acceptable acid salt is a hydrochloride.

8. A pharmaceutical composition comprising at least one compound according to claim 1, and at least one pharmaceutically acceptable excipient.

9. A process for preparing a compound having formula (I) according to claim 1, comprising:
a) reaction between an amine having the following formula (II), a halide having the following formula (III), and an aldehyde having the following formula (IV), wherein n and m, EAG, $R_1$, $R_2$ and A are as defined in claim 1 and X represents a halogen atom, to arrive at a compound having formula (I) according to claim 1, and b) optionally, formation of a pharmaceutically acceptable salt from the compound having formula (I) obtained in the previous step (a).

10. The process for preparing a compound having formula (I) according to claim 9, wherein the halide (III) and the amine (II) are first allowed to react with one another before adding the aldehyde (IV).

11. The process for preparing a compound having formula (I) according to claim 9, wherein X is a chlorine, bromine, or iodine atom.

12. A method for treating cancer, said method comprising administering to a patient suffering from cancer an effective amount of a compound according to claim 1, wherein said cancer is lung, breast, colon, rectal, kidney, skin, or bone cancer, or haematopoietic cancers, or tumours of neuroectodermal origin.

13. The method according to claim 12, wherein said haematopoietic cancer is leukaemia, myeloid leukaemia, lymphoma or bone marrow cancer.

14. The method according to claim 12, wherein said tumour of neuroectodermal origin is glioblastoma.

15. The method according to claim 12, wherein said compound is a compound having the following formula (Ia):

wherein:
A is a saturated or unsaturated, linear or branched hydrocarbon chain including 1 to 10 atoms of carbon; and
$R_1$ and $R_2$ each represent, independently from one another, a hydrogen atom, a CO—($C_1$-$C_6$)-alkyl, ($C_1$-$C_6$) alkyl, phenyl or phenyl-($C_1$-$C_6$)-alkyl group, or $R_1$ and $R_2$ form, together with the nitrogen atom bearing same, a 5- to 15-member heterocycle, optionally substituted by a ($C_1$-$C_6$) alkyl group;
including the stereoisomers and the mixtures thereof, or a pharmaceutically acceptable acid salt thereof.

16. The method according to claim 12, wherein said compound is a compound having the following formula (1):

or a pharmaceutically acceptable acid salt thereof.

17. The compound according to claim 1, wherein:
m is an integer from 0 to 2;
n is an integer from 0 to 2; and
m+n≥1.

18. The compound according to claim 4, wherein the radicals $R_1$ and $R_2$ form, together with the nitrogen atom bearing same, a 13-member heterocycle.

19. The compound according to claim 5, wherein A is a saturated linear hydrocarbon chain comprising 3 carbon atoms.

* * * * *